(12) United States Patent
Williams et al.

(10) Patent No.: US 6,514,245 B1
(45) Date of Patent: Feb. 4, 2003

(54) SAFETY CRYOTHERAPY CATHETER

(75) Inventors: Ronald Williams, Menlo Park, CA (US); James Joye, Los Gatos, CA (US); Richard S. Williams, Redwood City, CA (US); Timothy D. Holland, Los Gatos, CA (US)

(73) Assignee: Cryovascular Systems, Inc., Los Gatos, CA (US)

( * ) Notice: Subject to any disclaimer, the term of this patent is extended or adjusted under 35 U.S.C. 154(b) by 143 days.

(21) Appl. No.: 09/619,583

(22) Filed: Jul. 19, 2000

Related U.S. Application Data

(63) Continuation-in-part of application No. 09/268,205, filed on Mar. 15, 1999.

(51) Int. Cl.⁷ .............................. A61B 18/18
(52) U.S. Cl. ........................ 606/21; 128/898
(58) Field of Search ............... 606/20, 21, 22, 606/23, 26, 192, 194; 607/104; 604/96, 101, 104

(56) References Cited

U.S. PATENT DOCUMENTS

| | | | |
|---|---|---|---|
| 3,125,096 A | | 3/1964 | Antiles et al. |
| 3,630,203 A | * | 12/1971 | Sellinger et al. |
| 3,901,241 A | | 8/1975 | Allen, Jr. |

(List continued on next page.)

FOREIGN PATENT DOCUMENTS

| | | | |
|---|---|---|---|
| WO | WO 91/05528 | 5/1991 | |
| WO | WO 98/37822 | 9/1998 | ........... A61B/17/36 |
| WO | WO 98/38934 | 9/1998 | |
| WO | WO 00/42931 | 7/2000 | |
| WO | WO02/04042 A2 | 1/2002 | |
| WO | WO02/07625 A | 1/2002 | |
| WO | WO02/38091 A1 | 5/2002 | |

OTHER PUBLICATIONS

U.S. patent application No. 09/203,011 filed on Dec. 1, 1998 entitled: *Apparatus and Method for Cryogenic Inhibition of Hyperplasia*, Inventor(s): James Joye et al. (Atty. Docket No. 18468–000110US).

U.S. patent application No. 09/344,177 filed on Jun. 24, 1999 entitled: *Cryosurgical Catheter Inhibition of Hyperplasia*, Inventor(s): James Joye et al. (Atty. Docket No. 18468–000120US).

U.S. Provisional patent application No. 60/121,638 filed on Feb. 24, 1999 entitled: *Cryogenic Angioplasty Catheter*, Inventor(s): James Joye et al. (Atty. Docket No. 18468–000400US).

U.S. Provisional patent applicaiton No. 60/121,637 filed on Feb. 24, 1999 entitled: *Cryogenic Angioplasty Catheter*, Inventor(s): James Joye et al. (Atty. Docket No. 18468–000500US).

(List continued on next page.)

*Primary Examiner*—Roy D. Gibson
(74) *Attorney, Agent, or Firm*—Townsend Townsend & Crew LLP; Mark D. Barrish, Esq.

(57) ABSTRACT

Improved devices, systems, and methods for inhibiting hyperplasia in blood vessels provide controlled and safe cryotherapy treatment of a target portion within a body lumen of a patient. Efficacy of endoluminal cryogenic cooling can be enhanced by limiting cooling of target tissues using a thermal barrier disposed between a dual balloon cryotherapy catheter. Containment of both balloons can be monitored by applying a vacuum within a space between the first and second balloons, and by coupling the vacuum space to a fluid shutoff so as to inhibit flow of cryogenic fluid in response to a change in the vacuum space. Controlled cooling of the vessel can be improved by use of a nebulizer in fluid communication with a cryogenic liquid supply lumen and a gas supply lumen.

30 Claims, 10 Drawing Sheets

U.S. PATENT DOCUMENTS

| | | | |
|---|---|---|---|
| 4,275,734 A | * | 6/1981 | Mitchiner |
| 4,336,691 A | | 6/1982 | Burnstein et al. |
| 4,754,752 A | | 7/1988 | Ginsburg et al. |
| 4,946,460 A | * | 8/1990 | Merry et al. .................. 606/24 |
| 5,019,075 A | | 5/1991 | Spears et al. |
| 5,041,089 A | | 8/1991 | Mueller et al. |
| 5,078,713 A | | 1/1992 | Varney |
| 5,092,841 A | | 3/1992 | Spears |
| 5,101,636 A | * | 4/1992 | Lee et al. .................... 62/48.1 |
| 5,106,360 A | | 4/1992 | Ishiwara et al. |
| 5,117,870 A | * | 6/1992 | Goodale et al. ......... 137/636.1 |
| 5,147,355 A | | 9/1992 | Friedman et al. |
| 5,151,100 A | | 9/1992 | Abele et al. |
| 5,190,539 A | | 3/1993 | Fletcher et al. |
| 5,191,883 A | | 3/1993 | Lennox et al. |
| 5,196,024 A | | 3/1993 | Barath |
| 5,275,595 A | | 1/1994 | Dobak, III |
| 5,342,301 A | * | 8/1994 | Saab ..................... 604/103.13 |
| 5,383,853 A | | 1/1995 | Jung et al. |
| 5,458,612 A | | 10/1995 | Chin |
| 5,486,208 A | | 1/1996 | Ginsburg |
| 5,501,681 A | | 3/1996 | Neuwirth et al. |
| 5,545,195 A | | 8/1996 | Lennox et al. |
| 5,617,739 A | | 4/1997 | Little |
| 5,644,502 A | | 7/1997 | Little |
| 5,667,521 A | | 9/1997 | Keown |
| 5,733,280 A | | 3/1998 | Avitall |
| 5,814,040 A | * | 9/1998 | Nelson et al. .................. 606/9 |
| 5,820,626 A | * | 10/1998 | Baumgardner ................ 606/13 |
| 5,846,235 A | * | 12/1998 | Pasricha et al. .............. 606/23 |
| 5,868,735 A | * | 2/1999 | Lafontaine ................... 606/21 |
| 5,899,898 A | | 5/1999 | Arless et al. .................. 606/22 |
| 5,899,899 A | | 5/1999 | Arless et al. .................. 606/22 |
| 5,902,299 A | * | 5/1999 | Jayaraman ............. 604/101.05 |
| 5,971,979 A | | 10/1999 | Joye et al. ..................... 606/21 |
| 6,027,499 A | * | 2/2000 | Johnston et al. .............. 606/22 |
| 6,235,019 B1 | * | 5/2000 | Lehmann et al. ............. 606/22 |
| 6,241,718 B1 | | 6/2001 | Arless et al. ............... 604/509 |
| 6,290,696 B1 | | 9/2001 | Lafontaine |
| 6,379,378 B1 | | 4/2002 | Werneth et al. |

OTHER PUBLICATIONS

U.S. patent application No. 09/268,205 filed Mar. 15, 1999 entitled: *Cryosurgical Fluid Supply*, Inventor(s): James Joye et al. (Atty. Docket No. 18468–000600US).

Meinhard Nebulizer, "The Meinhard® Concentric Glass Nebulizer," http://www.meinhard.com/product3.htm. pp. 1–2.

CMS Website Information "Cryomedical Science Introduces Cryolite®" http://www.cryomedical.com/R&D/crolite.htm (Nov. 22, 1998), 3 pages total.

CMS Website Information "Cell Suicide Following Cryosurgery" http://www.cryomedical.com/R&D/apoptosi.htm (Mar. 8, 1999), 3 pages total.

* cited by examiner

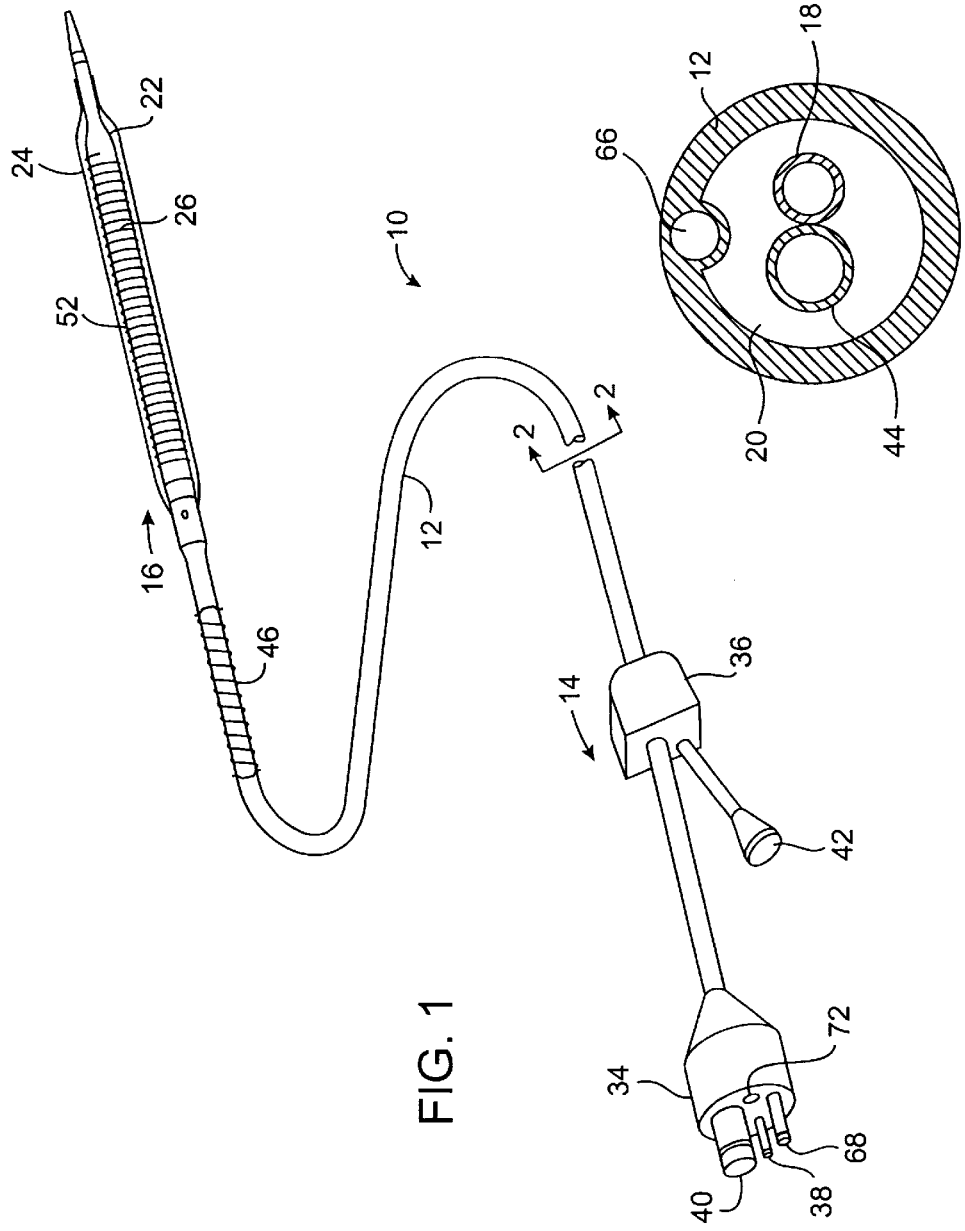

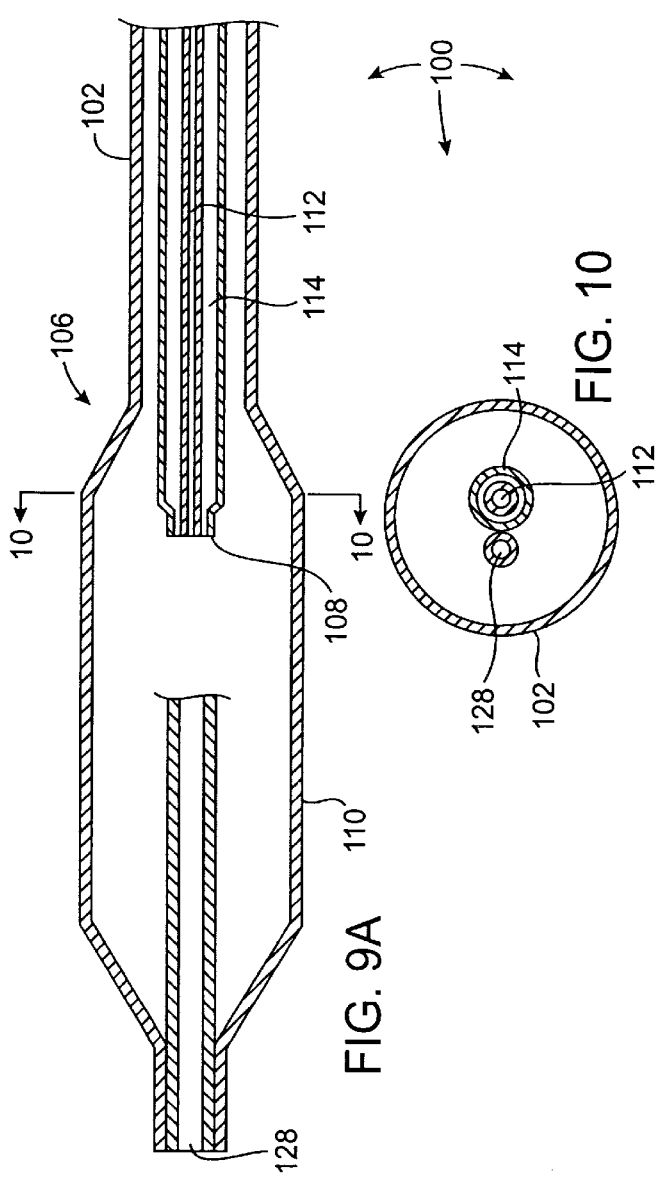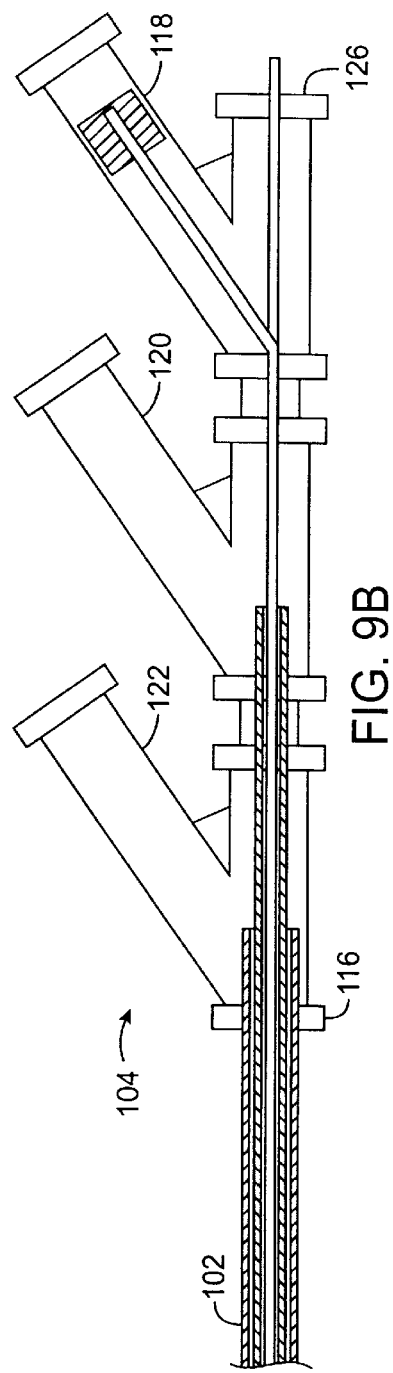

SAFETY CRYOTHERAPY CATHETER

CROSS-REFERENCES TO RELATED APPLICATIONS

This application is a Continuation-In-Part of co-pending U.S. patent application Ser. No. 09/268,205, filed Mar. 15, 1999, which is incorporated herein by reference.

BACKGROUND OF THE INVENTION

1. Field of the Invention

The present invention relates generally to apparatus and methods for inhibiting restenosis in blood vessels following angioplasty or other intravascular procedures for treating atherosclerosis and other diseases of the vasculature. More particularly, the present invention provides improved apparatus and methods for cryogenically treating a lesion within a patient's vasculature to inhibit hyperplasia (which often occurs after intravascular procedures).

A number of percutaneous intravascular procedures have been developed for treating atherosclerotic disease in a patient's vasculature. The most successful of these treatments is percutaneous transluminal angioplasty (PTA). PTA employs a catheter having an expansible distal end, usually in the form of an inflatable balloon, to dilate a stenotic region in the vasculature to restore adequate blood flow beyond the stenosis. Other procedures for opening stenotic regions include directional arthrectomy, rotational arthrectomy, laser angioplasty, stents and the like. While these procedures, particularly PTA and stenting, have gained wide acceptance, they continue to suffer from the subsequent occurrence of restenosis.

Restenosis refers to the re-narrowing of an artery within weeks or months following an initially successful angioplasty or other primary treatment. Restenosis typically occurs within weeks or months of the primary procedure, and may affect up to 50% of all angioplasty patients to some extent. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While these proposal have enjoyed varying levels of success, no one of these procedures is proven to be entirely successful in avoiding all occurrences of restenosis and hyperplasia.

It has recently been proposed to prevent or slow reclosure of a lesion following angioplasty by remodeling the lesion using a combination of dilation and cryogenic cooling. Co-pending U.S. patent application Ser. No. 09/203,011, filed Dec. 1, 1998, the full disclosure of which is incorporated herein by reference, describes an exemplary structure and method for inhibiting restenosis using a cryogenically cooled balloon. While these proposals appear promising, the described structures and methods for carrying out endovascular cryogenic cooling would benefit from still further improvements. In particular, work in connection with the present invention has shown that the antiproliferative efficacy of endoluminal cryogenic systems can be quite sensitive to the temperature to which the tissues are cooled.

Although cryogenic cooling shows great promise for endovascular use, it can be challenging to safely and reproducibly effect the desired controlled cooling. For example, many potential cryogenic fluids, such as liquid nitrous oxide, exhibit high levels of heat transfer. This is problematic as high cooling temperatures may kill the cooled cells (cell necrosis) rather than provoking the desired antiproliferative effect of endoluminal cryotherapy. Work in connection with present invention suggests that other cryogenic fluids, such as the AZ-50™ fluorocarbons (which may exhibit more ideal temperature characteristics), may raise biocompatibility and safety concerns. Additionally, improved safety measures to minimize any leakage of even biocompatible cryogenic fluids into the blood stream would be beneficial. Further, cryogenic systems that result in liquid vaporization within the balloon surface can decrease the temperature to which tissues are cooled and thus reduce the efficacy in inhibiting hyperplasia.

For these reasons, it would be desirable to provide improved devices, systems, and methods for treatment of restenosis and hyperplasia in blood vessels. It would be particularly desirable if these improved devices, systems, and methods were capable of delivering treatment in a very controlled and safe manner so as to avoid overcooling and/or injury to adjacent tissue. These devices, systems, and methods should ideally also inhibit hyperplasia and/or neoplasia in the target tissue with minimum side effects. At least some of these objectives will be met by the invention described herein.

2. Description of the Background Art

A cryoplasty device and method are described in WO 98/38934. Balloon catheters for intravascular cooling or heating a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336,691. A body cooling apparatus is described in U.S. Pat. No. 3,125,096. Rapid exchange catheters are described in U.S. Pat. Nos. 5,383,853 and 5,667,521. A MEINHARD® nebulizer is described at http://www.meinhard.com/product3.htm. The following U.S. Patents may also be relevant to the present invention: U.S. Pat. No. 5,458,612; 5,545,195; and 5,733,280.

The full disclosures of each of the above references are incorporated herein by reference.

SUMMARY OF THE INVENTION

The present invention provides improved devices, systems, and methods for inhibiting hyperplasia in blood vessels. The blood vessels will often be treated for atherosclerotic or other diseases by balloon angioplasty, arthrectomy, rotational arthrectomy, laser angioplasty, stenting, or another primary treatment procedure.

Inhibition of excessive cell growth is desirable when such treatments are employed so as to reduce and/or eliminate any associated hyperplasia and to maintain the patency of a body lumen. The present invention allows for cryotherapy treatment of a target portion within the body lumen of a patient in a very controlled and safe manner, particularly when using fluid capable of cooling tissues below a target temperature range.

In a first aspect, the invention provides a cryotherapy catheter comprising a catheter body having a proximal end and a distal end with a cooling fluid supply lumen and an exhaust lumen extending therebetween. A first balloon is disposed near the distal end of the catheter body in fluid communication with the supply and exhaust lumens. A second balloon is disposed over the first balloon with a thermal barrier therebetween.

Treatment according to this first aspect of the present invention can be effected by positioning the first balloon within the blood vessel adjacent a target portion. The "target portion" will often be a length within the blood vessel which is at risk of hyperplasia, typically as a result of balloon angioplasty (or some other treatment). Cryogenic cooling fluid is introduced into the first balloon (in which it often vaporizes) and exhausted. The second balloon expands to radially engage the vessel wall. The target portion is cooled to a temperature which is sufficiently low for a time which is sufficiently long to inhibit excessive cell proliferation. Heat transfer will be inhibited between the first and second balloons by the thermal barrier so as to limit cooling of the target portion. The inhibited cooling treatment will be directed at all or a portion of a circumferential surface of the body lumen, and will preferably result in cell growth inhibition, but not necessarily in significant cell necrosis. Particularly in the treatment of arteries before, during, and/or following balloon angioplasty, cell necrosis may be undesirable if it increases the hyperplastic response. Thus, the present invention will cool target tissue to a limited cooling temperatures to slow or stop cell proliferation.

The thermal barrier may comprise a gap maintained between the balloons by a filament. The filament typically comprises a helically wound, braided, woven, or knotted monofilament. The thermal barrier may also comprise a gap maintained between the balloons by a plurality of bumps on an outer surface of the first balloon or an inner surface of the second balloon. Alternatively, the thermal barrier may comprise a sleeve. The sleeve can be solid or perforated. The catheter of the present invention may also be equipped with a guidewire lumen that extends axially outside the exhaust lumen to minimize the occurrence of cryogenic fluid entering the blood stream via the guidewire lumen.

Suitable cryogenic fluids will preferably be non-toxic and include liquid nitrous oxide, liquid carbon dioxide, and the like. The balloons are preferably inelastic and have a length of at least 1 cm each, more preferably in the range from 2 cm to 5 cm each. The balloons will have diameters in the range from 2 mm to 5 mm each in a coronary artery and 2 mm to 10 mm each in a peripheral artery. Generally, the temperature of the outer surface of the first balloon will be in a range from about 0° C. to about −50° C. and the temperature of the outer surface of the second balloon will be in a range from about −3° C. to about −15° C. This will provide a treatment temperature in a range from about −3° C. to about −15° C. The tissue is typically maintained at the desired temperature for a time period in the range from about 1 to 60 seconds, preferably being from 20 to 40 seconds. Hyperplasia inhibiting efficacy may be enhanced by repeating cooling in cycles, typically with from about 1 to 3 cycles, with the cycles being repeated at a rate of about one cycle every 60 seconds.

In another aspect, the invention provides a cryotherapy system comprising an elongate body having a proximal end and a distal end with a fluid supply and exhaust lumen extending therebetween. A first balloon defines a volume in fluid communication with the supply and exhaust lumens. A fluid shutoff is coupled to a cryogenic fluid supply with the supply lumen. A second balloon is disposed over the first balloon with a vacuum space therebetween. The vacuum space is coupled to the fluid shutoff so as to inhibit flow of cryogenic fluid into the first balloon in response to a change in the vacuum space.

Advantageously, the cryotherapy system can monitor the integrity of both balloons during cooling to ensure that no cryogenic fluid is escaping from the first balloon or blood entering from the second balloon. Further, in the event of a failure, the fluid shutoff can prevent the delivery of additional cryogenic fluid into the supply lumen while the second balloon acts to contain any cryogenic fluid that may have escaped the first balloon.

The fluid shutoff typically comprises a vacuum switch connected to a shutoff valve by a circuit, the circuit being powered by a battery. The switch may remain closed only when a predetermined level of vacuum is detected in the second balloon. The closed switch allows the shutoff valve (in fluid communication with the cryogenic fluid supply) to be open. Alternatively, the circuit may be arranged so that the switch is open only when the predetermined vacuum is present, with the shutoff valve being open when the switch is open. The vacuum is reduced when either the first balloon is punctured, allowing cryogenic fluid to enter the vacuum space, or the second balloon is punctured, allowing blood to enter the vacuum space. The vacuum may be provided by a simple fixed vacuum chamber coupled to the vacuum space by a vacuum lumen of the catheter body, or may be applied with a simple positive displacement pump, the pump optionally similar to a syringe. Still further vacuum means might be used, including cryogenic vacuum pumps and the like. The cryogenic fluid supply and battery may be packaged together in a detachable energy pack. A plurality of separate replaceable energy packs allow for multiple cryogenic fluid cooling cycles. The system may additionally comprises a hypsometer with a thermocouple, thermistor, or the like, located in the first balloon to determine the pressure and/or temperature of fluid in the first balloon.

In another aspect, the present invention provides a cryotherapy catheter comprising a catheter body having a proximal end and a distal end with a nebulizer disposed adjacent the distal end. A first balloon is disposed on the distal end of the catheter body. The inner surface of the first balloon is in fluid communication with the nebulizer.

The nebulizer may comprise at least one port in fluid communication with a liquid supply lumen and a gas supply lumen. The liquid supply lumen may further be coaxial with the gas supply lumen. Thus, the nebulizer can introduce a liquid and gas mixture into the first balloon so that pressure and the enthalpy of vaporization of a safe cryogenic fluid within the balloon surface can be independently selected and/or controlled. This in turn allows for improved temperature control of the cryogenic fluid.

Another aspect of the present invention is a method for treating a target portion of a blood vessel. The method comprises positioning a balloon within the blood vessel adjacent the target portion, introducing a cryogenic cooling fluid into the balloon, and exhausting the cooling fluid. The target portion is cooled to a temperature and for a time sufficient to inhibit subsequent cell growth. The blood vessel is a peripheral artery subject to hyperplasia resulting from a primary treatment. Suitable peripheral arteries which may benefit from these treatments include arteries of the legs, kidneys, renal, iliac, popliteal, and preferably superficial femoral arteries.

In yet another aspect, the invention provides a method for treating a target portion of a blood vessel. The method comprises positioning a first balloon within the blood vessel adjacent the target portion, introducing a cryogenic cooling fluid into the first balloon, and exhausting the cooling fluid. A second balloon disposed over the first balloon is expanded to radially engage the vessel wall. The target portion is cooled to a temperature and for a time sufficient to inhibit subsequent cell growth. Heat transfer between the first and second balloons is inhibited so as to limit cooling of the target portion.

In another aspect, the invention provides method for treating a target portion of a blood vessel. The method comprises positioning a first balloon within the blood vessel adjacent the target portion, introducing a cryogenic cooling fluid into the first balloon, and exhausting the cooling fluid. A second balloon disposed over the first balloon is expanded to radially engage the vessel wall. The target portion is cooled to a temperature and for a time sufficient to inhibit subsequent cell growth. Containment of the first and second balloons is monitored during cooling.

In another aspect, the invention provides a method for treating a target portion of a blood vessel. The method comprises positioning a balloon within the blood vessel adjacent the target portion, introducing a cryogenic liquid and gas mixture into the balloon with a nebulizer, and exhausting the cryogenic liquid and gas mixture. The target portion is cooled to a temperature and for a time sufficient to inhibit subsequent cell growth.

BRIEF DESCRIPTION OF THE DRAWINGS

FIG. 1 illustrates a cryotherapy catheter constructed in accordance with the principles of the present invention.

FIG. 2 is a cross-sectional view of the catheter taken along lines 2—2 in FIG. 1.

FIGS. 9A–9B illustrate cross sectional views of a distal and proximal end of an another cryotherapy catheter constructed in accordance with the principles of the present invention.

FIG. 10 is another cross-sectional view of the catheter taken along lines 10—10 in FIG. 9A.

DESCRIPTION OF THE SPECIFIC EMBODIMENTS

Figure 3A:
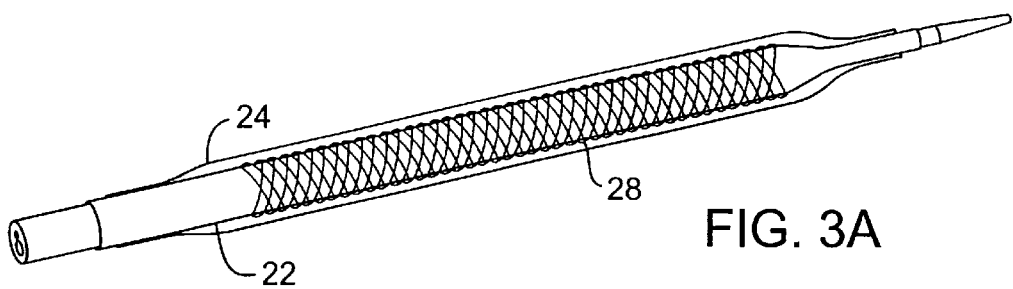
FIGS. 3A–3C illustrate the distal end of the cryotherapy catheter constructed in accordance with the principles of the present invention with the various thermal barrier configurations.

The present invention provides improved cryotherapy devices, systems, and methods for inhibiting hyperplasia in blood vessels. An exemplary cryotherapy catheter 10 constructed in accordance with the principles of the present invention is illustrated in FIGS. 1 and 2. The catheter 10 comprises a catheter body 12 having a proximal end 14 and a distal end 16 with a cooling fluid supply lumen 18 and an exhaust lumen 20 extending therebetween. A first balloon 22 is disposed near the distal end of the catheter body 12 in fluid communication with the supply and exhaust lumens. A second balloon 24 is disposed over the first balloon 22 with a thermal barrier 26 therebetween.

The balloons 22, 24 may be an integral extension of the catheter body 12, but such a structure is not required by the present invention. The balloons 22, 24 could be formed from the same or a different material as the catheter body 12 and, in the latter case, attached to the distal end 16 of the catheter body 12 by suitable adhesives, heat welding, or the like. The catheter body 12 may be formed from conventional materials, such as polyethylenes, polyimides, and copolymers and derivatives thereof. The balloons 22, 24 may also be formed from conventional materials used for angioplasty, preferably being inelastic, such as polyethylene terephthalate (PET), polyethylene, or other medical grade material suitable for constructing a strong non-distensible balloon. Additionally, balloons 22 and 24 could be formed from different material to provide improved protection. For example, the first balloon 22 could be formed from PET to provide strength while the second balloon 24 could be formed from polyethylene to provide durability. The balloons 22, 24 have a length of at least 1 cm each, more preferably in the range from 2 cm to 5 cm each. The balloons 22, 24 will have diameters in the range from 2 mm to 5 mm each in a coronary artery and 2 mm to 10 mm each in a peripheral artery.

Figure 3B:
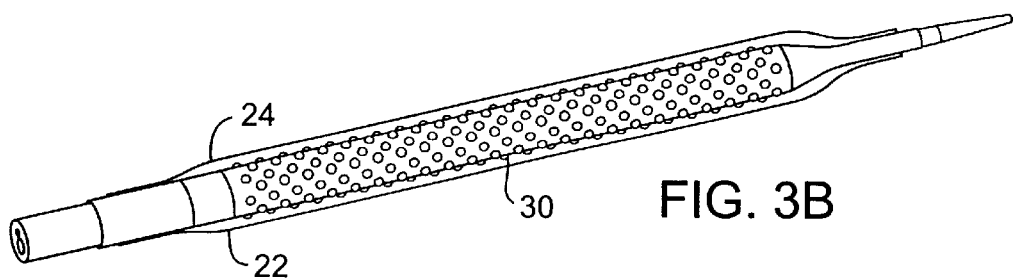
Figure 3C:
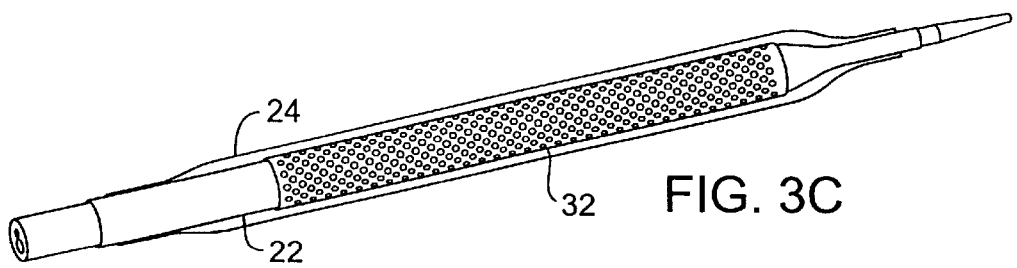

The thermal barrier 26 may comprise a gap maintained between the balloons 22, 24 by a filament 28, as shown in FIG. 3A. The filament typically comprises a helically wound, braided, woven, or knotted monofilament. The monofilament may be formed from PET or polyethylene napthlate (PEN), and affixed to the first balloon 22 by adhesion bonding, heat welding, fasteners, or the like. The thermal barrier 26 may also comprise a gap maintained between the balloons 22, 24 by a plurality of bumps 30 on an outer surface of the first balloon 22, as shown in FIG. 3B, and/or an inner surface of the second balloon 24. The plurality of bumps 30 may be formed in a variety of ways. For example, the bumps 30 may be intrinsic to the balloon (created during balloon blowing), or the bumps 30 could be created by deforming the material of the balloon wall, by affixing mechanical "dots" to the balloon using adhesion bonding, heat welding, fasteners, or the like. Alternatively, the thermal barrier 26 may comprise a gap maintained between the balloons 22, 24 by a sleeve 32, as shown in FIG. 3C. The sleeve 32 may be perforated and formed from PET or rubbers such as silicone and polyurathane.

Hubs 34 and 36 are secured to the proximal end 14 of the catheter body 12. Hub 34 provides a port 38 for connecting a cryogenic fluid source to the fluid supply lumen 18 which is in turn in fluid communication with the inner surface of the first balloon 22. Hub 34 further provides a port 40 for exhausting the cryogenic fluid which travels from balloon 22 in a proximal direction through the exhaust lumen 20. Hub 36 provides a port 42 for a guidewire which extends through a guidewire lumen 44 in the catheter body 12. Typically, the guidewire lumen 44 will extend through the exhaust lumen 20, as shown in FIG. 2. The guidewire lumen 44 may also extend axially outside the exhaust lumen 20 to minimize the occurrence of cryogenic fluid entering the blood stream via the guidewire lumen 44. Optionally, the guidewire lumen 44 may extend outside the inner surface of the first balloon 22 or the guidewire lumen 44 may allow for a guidewire to extend outside both balloons 22, 24. Additionally, a reinforcing coil 46 may extend along the catheter body 12 proximal the first balloon 22. The reinforcing coil 46 may comprise a simple spring having a length typically in the range from 6 cm to 10 cm to prevent the catheter 10 from kinking up inside the blood vessel.

Figure 4B:
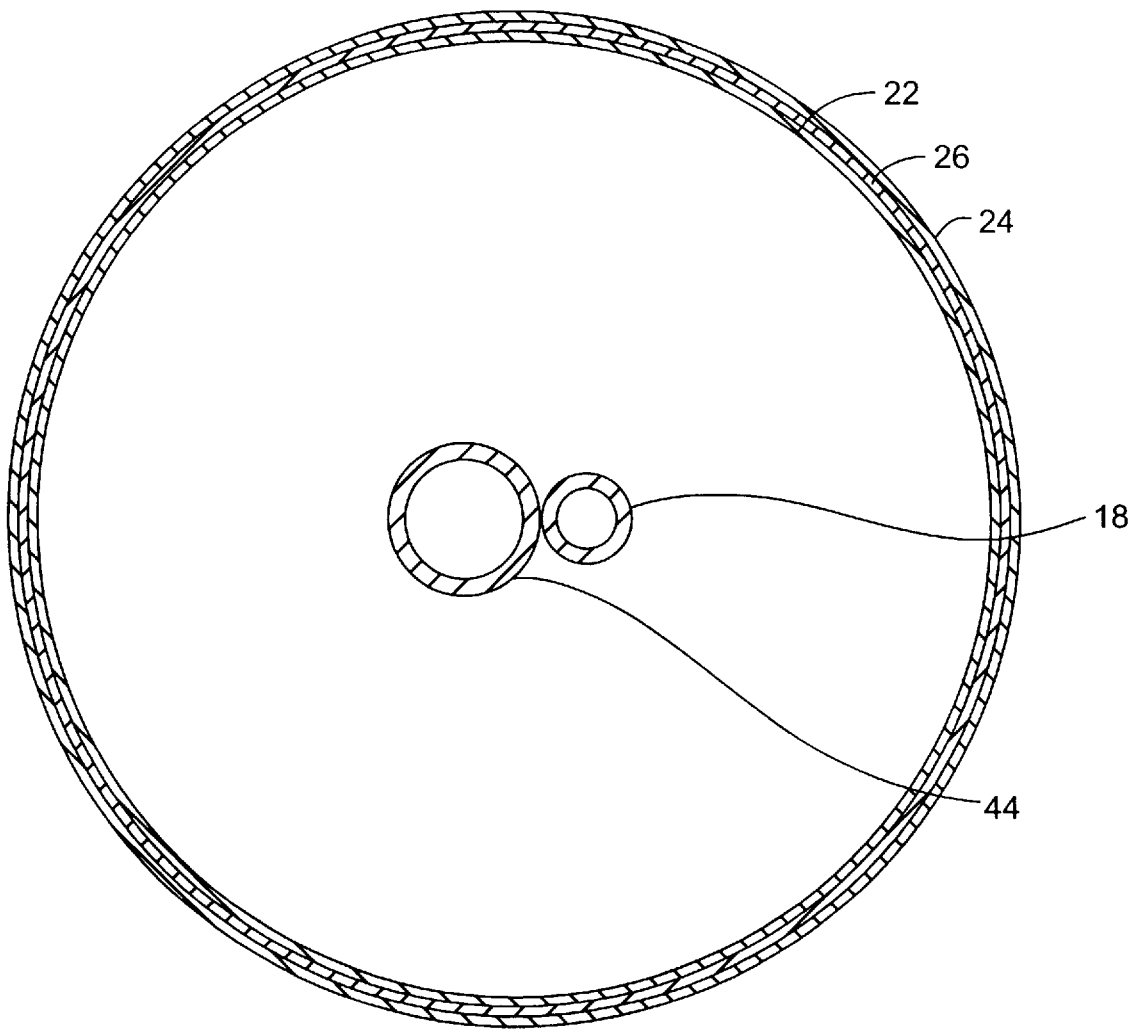
FIGS. 4A–4B illustrate cross-sectional views of the distal end of the cryotherapy catheter before and after balloon expansion.
Figure 4A:
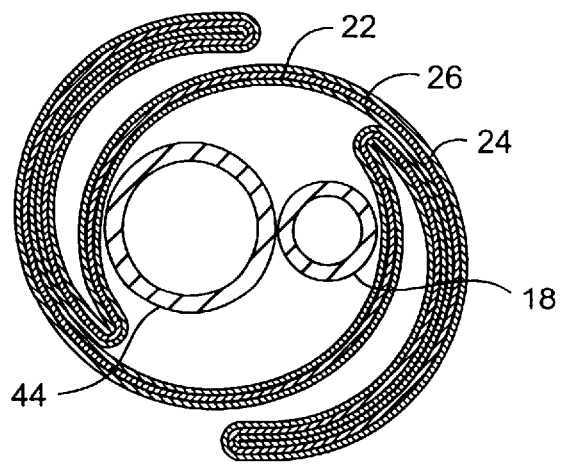

In operation, treatment will be effected by positioning the first balloon 22 within the blood vessel adjacent a target portion. FIG. 4A illustrates a cross-sectional view of the distal end of the cryotherapy catheter during positioning. Cryogenic cooling fluid is introduced into the first balloon 22 (in which it often vaporizes) and exhausted. The second balloon 24 expands to radially engage the vessel wall. The vaporized fluid serves both to inflate balloon 22 (and expand balloon 24) and to cool the exterior surface of the balloons 22, 24. FIG. 4B illustrates a cross-sectional view of the distal end of the cryotherapy catheter after the balloons expand. The target portion is cooled to a temperature which is sufficiently low for a time which is sufficiently long to inhibit excessive cell proliferation. Heat transfer will be inhibited between the first and second balloons 22, 24 by the thermal barrier 26 so as to limit cooling of the target portion to a desired temperature profile. The inhibited cooling treatment will be directed at all or a portion of a circumferential surface of a body lumen, and will preferably result in cell growth inhibition.

Figure 5:
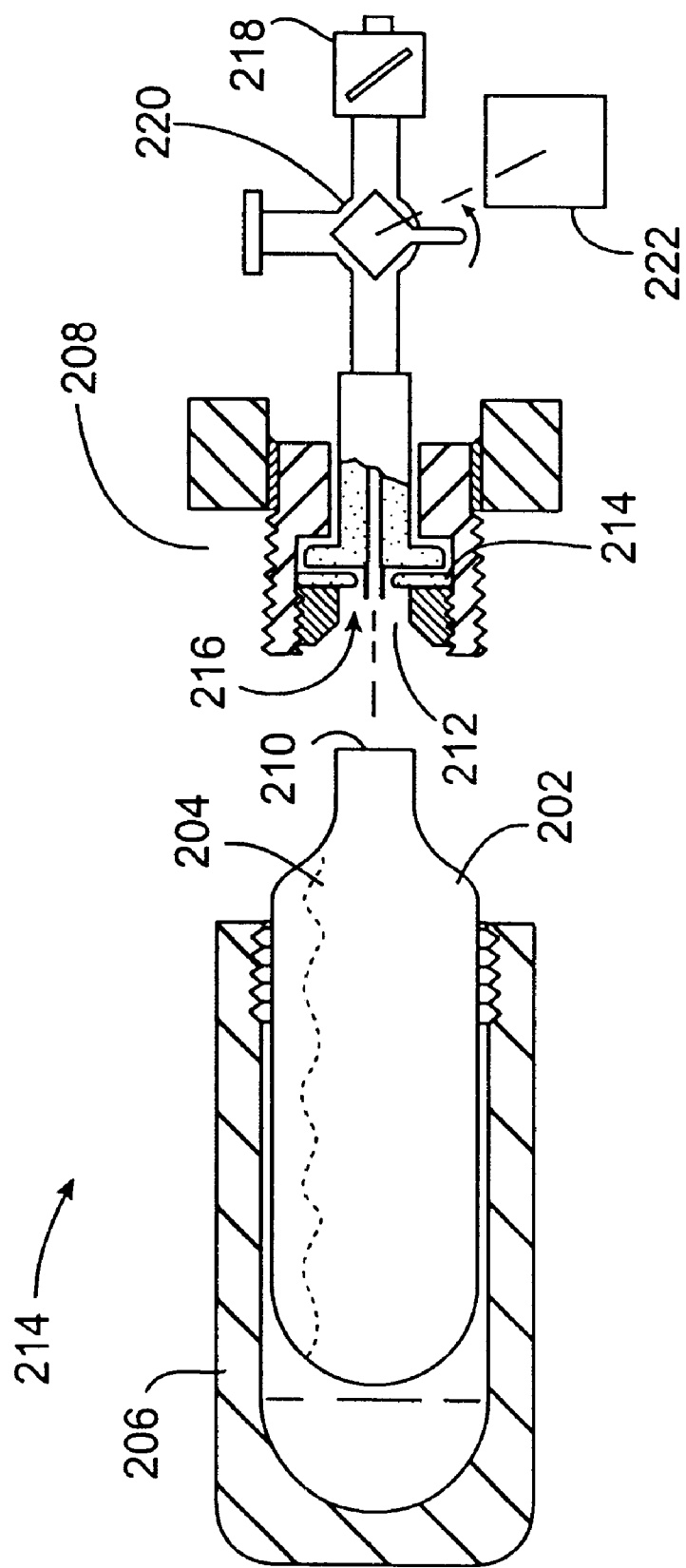
FIG. 5 is an exploded cross-sectional view of a cryogenic fluid supply system for use in the cryotherapy catheter of FIG. 1.

Suitable cryogenic fluids will preferably be non-toxic and may include liquid nitrous oxide, liquid carbon dioxide, and the like. A cryogenic fluid delivery system 214 (which was more fully described in parent application Ser. No. 09/268,205, the full disclosure of which has been previously incorporated herein by reference) is illustrated in FIG. 5. Delivery system 214 makes use of a disposable cartridge 202 containing a cryogenic fluid 204. Cartridge 202 is received in a casing 206, and the casing threadably engages a fitting 208. By placing cartridge 202 in casing 206 and threading fitting 208 to the casing, a frangible seal 210 of the cartridge can be breached by a protruding tube 212 of the fitting. Fitting 208 may include a sealing body such as a rubber washer 214 to avoid leakage of cooling fluid 204, while the fitting and casing 206 may include gripping surfaces to facilitate breaching seal 210.

Once seal 210 has been breached by fitting 208, cryogenic cooling fluid 204 passes through a lumen 216 through the fitting and on toward the balloon surface. Coupling of fluid delivery system 214 to catheter 10 is facilitated by including a detachable connector 218 along the cooling fluid flow path, the connector typically comprising a luer fitting which sealingly engages fluid supply port 38 of the catheter. While connector 218 is here shown closely coupled to fitting 208, it should be understood that the fluid flow path may follow a longer, and optionally flexible path. In fact, aspects of the present invention will find uses with standard reusable cryogenic fluid supply system.

In fluid delivery system 214 illustrated in FIG. 5, a simple stopcock 220 is disposed between fitting 208 and connector 218. Stopcock 220 allows the cryogenic system operator to pierce seal 210 of cartridge 202 while setting up the system, and to later manually initiate flow of the cooling fluid by turning a lever of the stopcock. A port on stopcock 220 may be in fluid communication with the open cooling fluid path to verify cooling fluid pressure, temperature, or the like. Alternatively, the stopcock port may be isolated from the cooling fluid path when the stopcock opens.

Casing 206 and fitting 208 may comprise a variety of polymer and/or metallic materials. In the exemplary embodiment, casing 206 and at least a portion of fitting 208 are off-the-shelf items sized and adapted to receive and open a standard, commercially available pressurized fluid cartridge. The casing and seal opening components of the fitting may be fabricated by assembling and/or modifying components sold commercially by iSi Gmbh located in Vienna, Austria.

Cartridge 202 may be transported, stored, and optionally, used at room temperature. The cryogenic cooling fluid sealed within cartridge 202 may comprise $CO_2$, $N_2O$, AZ-50™ fluorocarbon, and/or a variety of alternative cryogenic cooling fluids. As these fluids are at quite high pressures within cartridge 202, they may be in the form of a liquid or gas/liquid mixture, even at room temperature. The pressure of cooling fluid 204 within cartridge 202 will often be greater than 400 psi, preferably being about 500 psi or more at room temperature. It should be understood that the cartridge pressure will decreased during the treatment as cooling fluid is consumed. Advantageously, the quantity of cooling fluid 204 may be such that the cryosurgical system (including cryogenic fluid supply 214 and catheter 10) cool and maintain a target tissue within a predetermined temperature range for a time within a predetermined time range by the time the cooling fluid is consumed from the canister. In other words, by selecting the proper fluid supply cartridge and catheter structures, the cryogenic therapy may be self-terminating without active intervention by an electronic control system, the operator, or the like. Cooling flow may cease when the fluid pressure within cartridge 202 is equal to ambient pressure, or may optionally be interrupted when the pressure drops below some threshold value.

Canister 202 will typically comprise a metallic structure. Suitable cartridges will hold quantities of cryogenic cooling fluid that are sufficient to cool the target tissue to the treatment temperature range for a time in the predetermined time range. Cartridges might have volumes between 2 cc and 100 cc (depending in part on the flash expansion temperatures of the cryogenic fluid), and may contain between about 5 g and 30 g of cooling fluid. A typical cartridge might contain a quantity of $N_2O$ in a range from about 5 ml to about 20 ml, ideally having about a 10 ml or 8 grams of $N_2O$ liquid at about 750 psi. Conveniently, such cartridges are commercially available for use in whipped cream dispensers. As explained below, canister 202 may be at room temperature or even chilled, but will preferably be warmed gently prior to use. It is preferred that the canister 202 is heated using a 20 watt to 50 watt, preferably 40 watt, Kapton heater film.

Although the above discussion occasionally refers to structures and techniques for enhancing the efficiency of cryogenic cooling, known cryogenic cooling techniques are capable of inducing temperatures well below the preferred treatment temperature ranges for use with the present invention. To moderate the cooling of the target tissue and provide antiproliferative benefits, the systems of the present invention may optionally rely on the thermal barrier 26, as described above with reference to FIG. 1. Alternatively, a motor 222 may drivingly engage stopcock 220 so as to intermittently interrupt the flow of cooling fluid to the balloon. By cycling of the cooling fluid flow on and off, the present invention takes advantage of the thermal transients of the cooling system to prevent the tissue from reaching the low temperatures associated with a steady state cooling flow.

A variety of structures might be used to intermittently interrupt the flow of cooling fluid to the cryotherapy catheter. In the embodiment of FIG. 5, an output shaft of an electrical motor assembly might be attached to a modified commercially available medical stopcock valve. Suitable motors might be powered from a standard wall outlet or batteries, and a reduction drive unit might be used to reduce the speed of the stopcock valve rotation to about one cycle per second. The drive motor may have a fixed speed to provide a temperature within a single predetermined temperature range, or may have a variable speed to actively control the temperature by varying the cycle speed, to alter the predetermined treatment temperature range for a particular treatment, and/or to provide the predetermined temperature range given a particular ambient condition, cryotherapy catheter configuration, and the like.

Use of a flow interrupter can be quite advantageous. For example, if cartridge 202 contains $N_2O$ at 750 psi, and if the cartridge is placed in an ice bath (thereby providing a convenient and reproducible initial condition), flash expansion of the cooling fluid to a pressure between atmospheric (14.7 psi) and 100 psi will result in cryogenic fluid temperatures in a range from about −45° C. to about −90° C. Such structures may be useful, for example, for therapies in which cryogenic ablation of tissues is desired. Surprisingly, it may be beneficial to gently warm the cartridge to enhance the fluid pressure and flow rate. Hence, alternative predetermined initial conditions might be provided by warming canister 202, preferably to about body temperature (with a hot plate, water bath, or the like) or even by holding the canister in a person's pocket (which may warm the canister to about 33° C.). Still further predetermined initial temperatures may simply comprise operating room temperature.

To provide apoptosis and/or programmed cell death so as to inhibit hyperplasia and/or neoplasia of a blood vessel related to angioplasty, stenting, rotational or directional artherectomy, or the like, it will often be desirable to provide more moderate cryogenic treatment temperatures. A wide variety of other therapies may also benefit from these treatment structures, including the formation of cryogenic lesions within the cardiac atrium for treatment of atrial fibrillation, and the like. As a particular example, the cardiac tissue ablation devices and methods described in PCT Patent Application WO 98/49957, published on Nov. 12, 1998 (the full disclosure of which is incorporated herein by reference) might benefit from treatment structures that provide temperatures significantly higher than about −30° C., in other words, significantly warmer than cooled tissue temperatures provided by many cryosurgical methods.

The cryogenic fluid will flow through the supply lumen 18 as a liquid at an elevated pressure and will vaporize at a lower pressure within the first balloon 22. For nitrous oxide, a delivery pressure within the supply lumen 18 will typically be in the range from 600 psi to 1000 psi at a temperature below the associated boiling point. After vaporization, the nitrous oxide gas within the first balloon 22 near its center will have a pressure typically in the range from 15 psi to 100 psi. Preferably, the nitrous oxide gas will have a pressure in the range from 50 psi to 100 psi in a peripheral artery and a range from about 15 psi to 45 psi in a coronary artery.

Generally, the temperature of the outer surface of the first balloon 22 will be in a range from about 0° C. to about −50° C. Preferably, the temperature of the outer surface of the first balloon 22 in a peripheral artery will be in a range from about 0° C. to about −40° C. The temperature of the outer surface of the second balloon 24 will be in a range from about −3° C. to about −15° C. This will provide a desired treatment temperature in a range from about −3° C. to about −15° C. The tissue is typically maintained at the desired temperature for a time period in the range from about 1 to 60 seconds, preferably being from 20 to 40 seconds. Hyperplasia inhibiting efficacy may be enhanced by repeating cooling in cycles, typically with from about 1 to 3 cycles, with the cycles being repeated at a rate of about one cycle every 60 seconds.

The cooling temperature may increase in both a radially outward direction and in both axial directions from the center of the balloons 22, 24 so that the temperature will be lowest near the center. Additionally, by extending the balloons 22, 24 by distances of at least 0.5 cm, preferably of at least 1 cm, in each direction from the center of the balloons, the temperatures at the ends of the balloons will generally be no lower than 0° C. In this way, a desired low temperature can be maintained at the outer surface of the balloons in a treatment region near the center of the balloons, while the distal and proximal ends of the balloons act to insulate the colder portions from non-target regions within the artery or other body lumen. It will be appreciated that the axial length of the treatment region of the balloons 22, 24 can also be varied considerably by varying the lengths of the balloons.

The cryotherapy catheter 10 in FIG. 1 additionally illustrates a safety mechanism that monitors the containment of the first and second balloons 22, 24. The first balloon 22 defines a volume in fluid communication with the supply and exhaust lumens. A fluid shutoff is coupled to a cryogenic fluid supply with the supply lumen 18. The second balloon 24 is disposed over the first balloon 22 with a vacuum space 52 therebetween. The vacuum space 52 is coupled to the fluid shutoff so as to inhibit flow of cryogenic fluid into the first balloon 22 in response to a change in the vacuum space 52.

Figure 6:
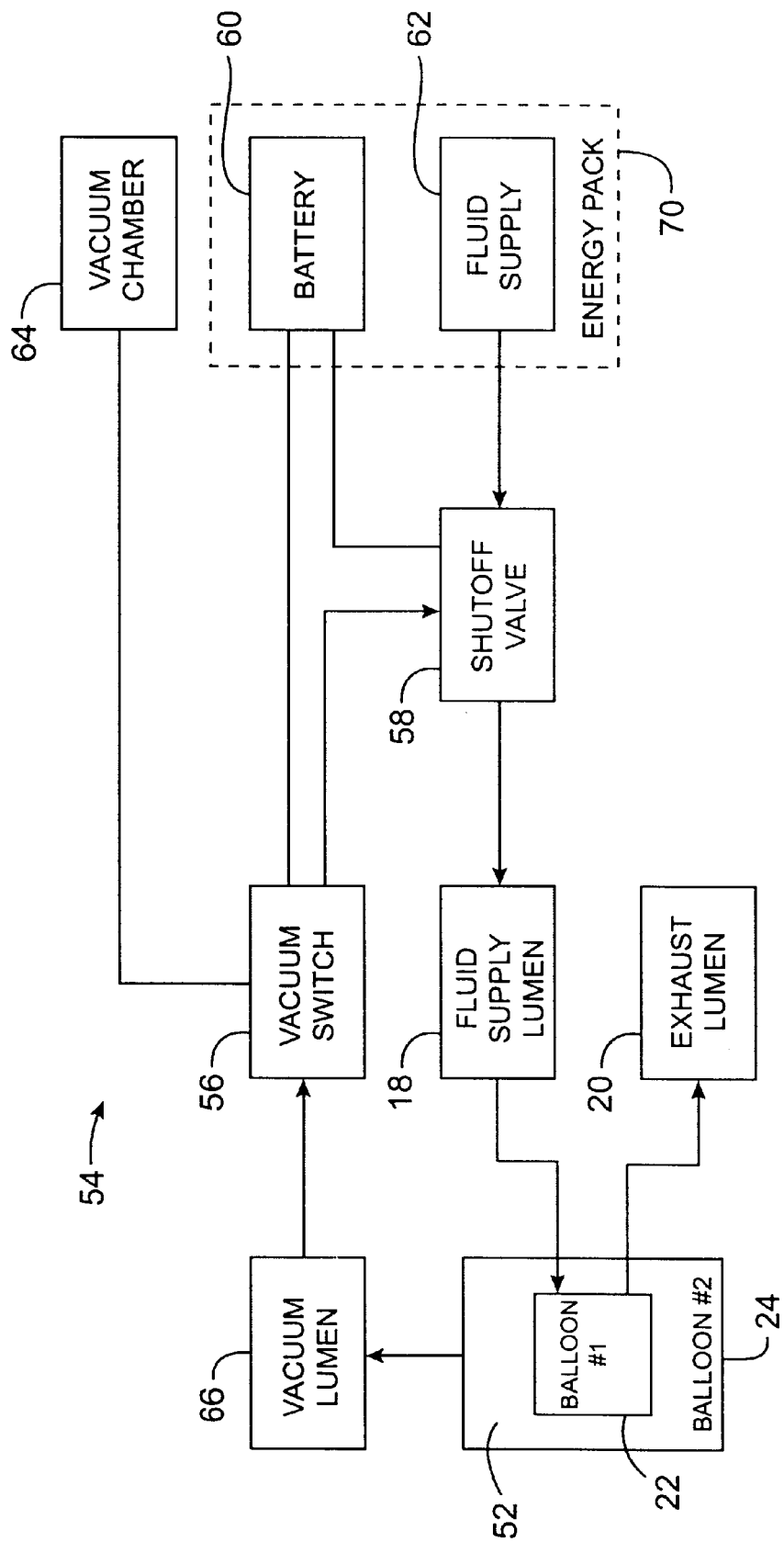
FIG. 6 is a functional flow diagram illustrating the operation of an automatic fluid shutoff mechanism of the catheter of FIG. 1.

FIG. 6 illustrates a functional flow diagram of the automatic fluid shutoff mechanism 54. The fluid shutoff 54 typically comprises a vacuum switch 56 connected to a shutoff valve 58 by a circuit, the circuit being powered by a battery 60. The switch 56 may remain closed only when a predetermined level of vacuum space 52 is detected in the second balloon 24. The closed switch 56 allows the shutoff valve 58, in fluid communication with the cryogenic fluid supply 62, to be open. Alternatively, the circuit may be arranged so that the switch 56 is open only when the predetermined vacuum space 52 is present, with the shutoff valve 58 being open when the switch is open. The vacuum space 52 is reduced when either the first balloon 22 is punctured, allowing cryogenic fluid to enter the vacuum space 52, or the second balloon 24 is punctured, allowing blood to enter the vacuum space 52. In addition to monitoring the containment of both balloons 22, 24, in the event of a failure, the vacuum switch 56 will be triggered to prevent the delivery of additional cryogenic fluid from the fluid supply 62 into the supply lumen 18. The second balloon 24 also acts to contain any cryogenic fluid that may have escaped the first balloon 22.

Figure 7:
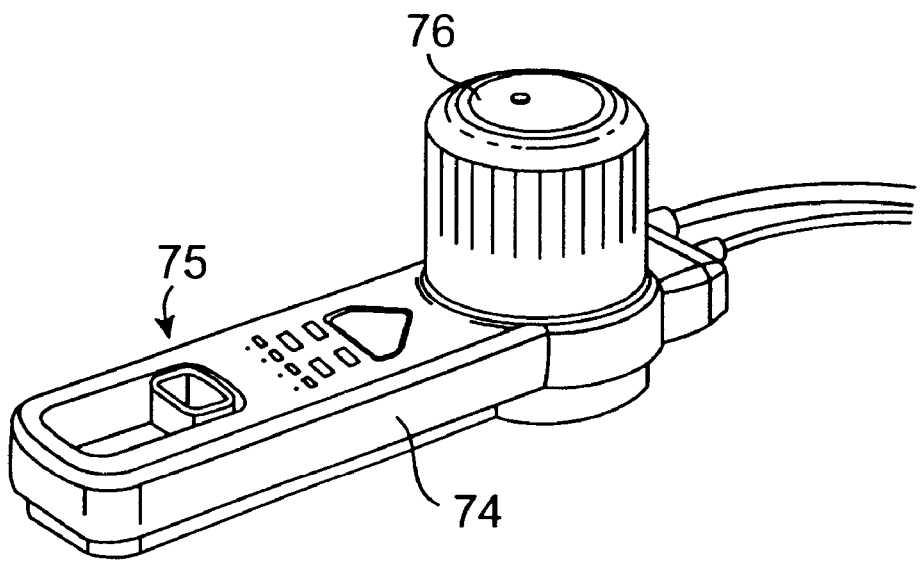
FIGS. 7 and 7A illustrate a handle and removable energy pack for use in the cryotherapy catheter of FIG. 1.
Figure 7A:
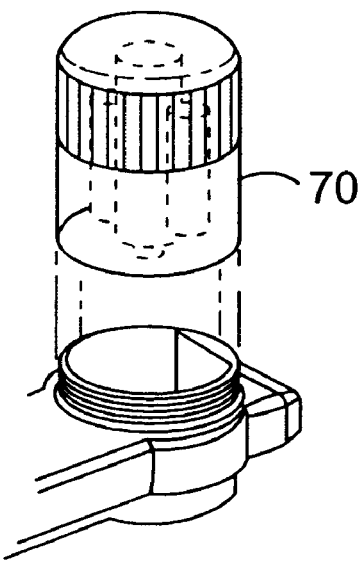

The vacuum space 52 may be provided by a simple fixed vacuum chamber 64 coupled to the vacuum space 52 by a vacuum lumen 66 of the body 12 via a vacuum port 68 (See FIG. 1). In the exemplary embodiment, a positive displacement pump (ideally being similar to a syringe) is disposed within handle 74 and may be actuated by actuator 75, as seen in FIG. 7. A latch may restrain actuator 75 to maintain the vacuum without having to hold the actuator manually. The vacuum space 52 should comprise a small volume of vacuum in the range from 1 mL to 100 mL, preferably 10 mL or less, as a smaller vacuum space 52 facilitates detection of a change in the amount of vacuum when a small amount of fluid leakage occurs. The cryogenic fluid supply 62 and battery 60 for powering the circuit may be packaged together in an energy pack 70, as seen in FIG. 7A. The energy pack 70 is detachable from a proximal handle 74 of the catheter body and disposable. A plurality of separate replaceable energy packs 70 allow for multiple cryogenic cooling cycles. Additionally, an audio alert or buzzer 76 may be located on the handle 74, with the buzzer providing an audio warning unless the handle is maintained sufficiently upright to allow flow from the fluid supply 62. The cryotherapy catheter may additionally comprise a hypsometer 72 coupled to the volume by a thermocouple, thermistor, or the like located in the first balloon 22 or handle to determine the pressure and/or temperature of fluid in the first balloon 22. The hypsometer allows for accurate real time measurements of variables (pressure, temperature) that effect the efficacy and safety of cryotherapy treatments.

Figure 8:
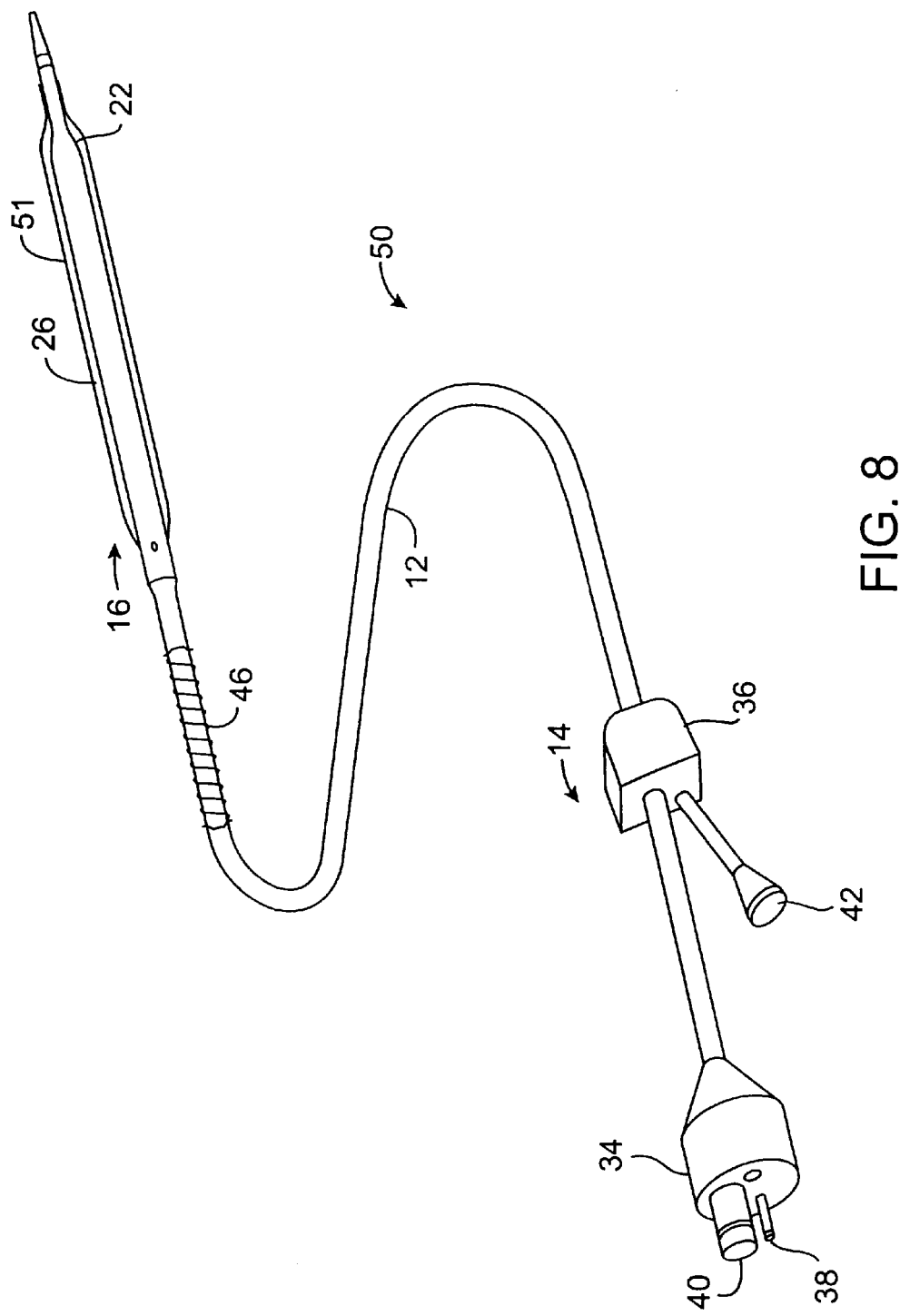
FIG. 8 illustrates another embodiment of the cryotherapy catheter constructed in accordance with the principles of the present invention.

Referring now to FIG. 8, an alternative cryotherapy catheter 50 will be described. The catheter 50 comprises a catheter body 12 having a proximal end 14 and a distal end 16 with a cooling fluid supply lumen 18 and an exhaust lumen 20 extending therebetween. A balloon 22 is disposed near the distal end of the catheter body 12 in fluid communication with the supply and exhaust lumens. An elastic membrane 51 is disposed over the balloon 22 with a thermal barrier 26 therebetween.

The elastic membrane 51 may be formed from polyurathane sold commercially by Polyzen located in Cary, North Carolina, to provide durability. The elastic membrane 51 has thickness typically in the range from 0.001 in. to 0.004 in., preferably 0.002 in., and may be multi-layered, from one to four layers, to provide additional insulation. The membrane 51 will have a resting diameter in the range from 2 mm to 6 mm, and may also aid in folding balloon 22 down to a low profile by providing a smaller membrane resting diameter than the balloon diameter. For example, a resting membrane diameter of 5.5 mm may be used with a balloon diameter of 6 mm. The membrane 51 is typically formed on mandrels and affixed to proximal and distal ends of the balloon by adhesion bonding, heat welding, fasteners, or the like.

With reference now to FIGS. 9A and 9B, cross sectional views of a distal and proximal end of an alternate cryotherapy catheter 100 are illustrated, with FIG. 10 showing another cross-sectional view of the catheter 100 taken along lines 10—10. The cryotherapy catheter 100 comprises a catheter body 102 having a proximal end 104 and a distal end 106 with a nebulizer 108 disposed adjacent the distal end 106. A first balloon 110 is disposed on the distal end 106 of the catheter body 102. The inner surface of the first balloon 110 is in fluid communication with the nebulizer 108. Advantageously, the nebulizer 108 can introduce a liquid and gas mixture into the first balloon 110 so that pressure and the enthalpy of vaporization of a safe cryogenic fluid within the balloon surface can be independently selected and/or controlled. This in turn allows for enhanced temperature control of the cryogenic fluid.

The nebulizer 108 may comprise at least one port in fluid communication with a liquid supply lumen 112 and a gas supply lumen 114. The liquid supply lumen 112 may further be coaxial the gas supply lumen 114. Optionally, the nebulizer 108 may comprise a plurality of liquid supply lumens coaxial the gas supply lumens, where the gas supply lumens adhere to an outerjacket covering. During nebulization, a portion of liquid from the liquid supply lumen 112 is atomized in the balloon 110 and another portion of liquid may return toward the proximal end 104 of the catheter body 102 from the balloon 110.

A hub 116 is secured to the proximal end 104 of the catheter body 102. Hub 116 provides a port 118 for connecting a cryogenic fluid source to the liquid supply lumen 112 which is in turn in fluid communication with the nebulizer 108. The hub 116 further provides a port 120 for connecting a cryogenic gas source to the gas supply lumen 114 which is in turn in fluid communication with the nebulizer 108. A third port 122 is provided for exhausting the cryogenic liquid and gas mixture which travels from balloon 110 in a proximal direction through an exhaust lumen. A forth port 126 is provided for a guidewire which extends through the guidewire lumen 128 in the catheter body 102. The guidewire lumen 128 may extend axially outside the liquid and gas supply lumens, as shown in FIG. 9, to minimize the occurrence of cryogenic fluid entering the blood stream via the guidewire lumen. Additionally, the catheter 100 may incorporate a reinforcing coil 46 (see FIG. 1) to prevent kinks, a second balloon configuration with a thermal barrier (see FIG. 1) to limit cooling, as well as a fluid shutoff mechanism (see FIG. 6) to ensure integrity of the cryotherapy system.

In operation, a balloon 110 is positioned within the blood vessel adjacent the target portion. A cryogenic liquid and gas mixture is introduced into the balloon with a nebulizer 108, and the cryogenic liquid (which often vaporizes in the balloon) and gas mixture are exhausted. The vaporized fluid serves both to inflate the balloon 110 and to cool the exterior surface of the balloon 110. The target portion is cooled to a temperature and for a time sufficient to inhibit subsequent cell growth.

The cryogenic liquid will flow through the supply lumen 112 at an elevated pressure and will vaporize at a lower pressure within the balloon 110. For nitrous oxide, a delivery pressure within the liquid supply lumen 112 will typically be in the range from 600 psi to 1000 psi at a temperature below the associated boiling point. For gaseous nitrous oxide, a delivery pressure within the gas supply lumen 114 will typically be in the range from 600 psi to 1000 psi. After liquid vaporization, the nitrous oxide gas within the balloon 110 near its center will have a pressure typically in the range from 15 psi to 100 psi. Generally, the temperature of the outer surface of the balloon 110 will be in a range from about −3° C. to about −15° C. This will provide a desired treatment temperature in a range from about −3° C. to about −15° C. The tissue is typically maintained at the desired temperature for a time period in the range from about 1 to 60 seconds, preferably being from 20 to 40 seconds. Hyperplasia inhibiting efficacy may be enhanced by repeating cooling in cycles, typically with from about 1 to 3 cycles, with the cycles being repeated at a rate of about one cycle every 60 seconds.

Figure 11A:
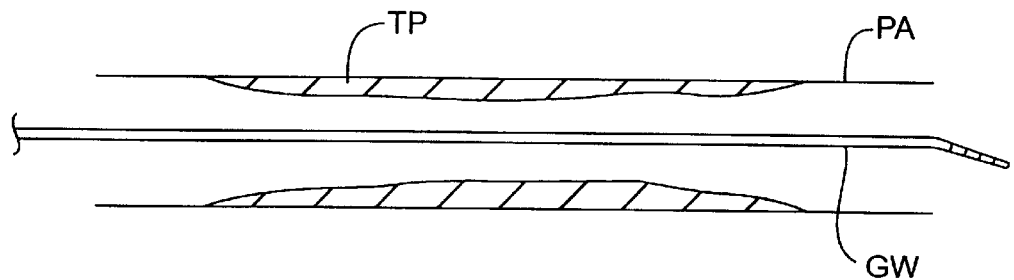
FIGS. 11A–11C schematically illustrate a method for using a cryotherapy catheter in a peripheral artery.
Figure 11B:
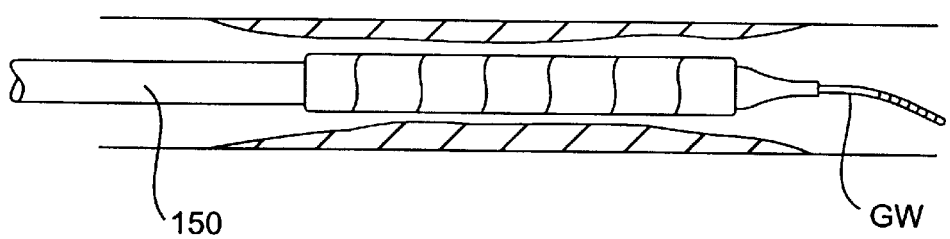
Figure 11C:
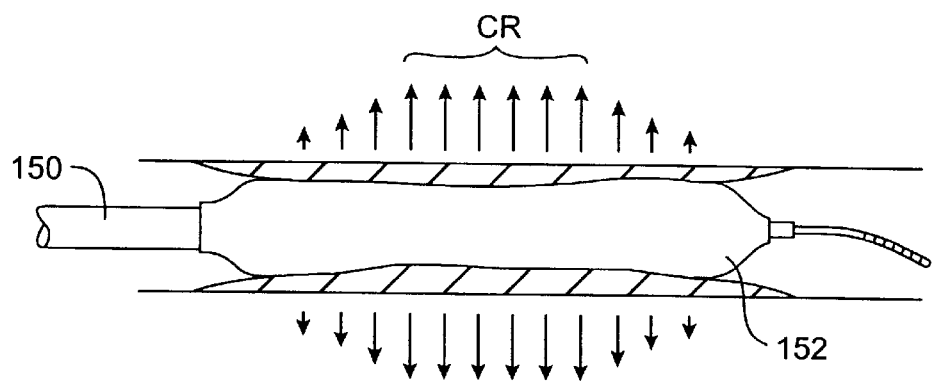

Referring now to FIGS. 11A through 11C, use of a cryotherapy catheter 150 for treating a target portion TP within a peripheral artery PA will be described. The target portion will usually have been previously treated by balloon angioplasty or other primary conventional protocol for treating atherosclerotic disease. Such primary treatment will typically utilize an intravascular catheter, which catheter will have been removed leaving a guidewire GW in place, as illustrated in FIG. 11A. A catheter 150 is then introduced over the guidewire, as illustrated in FIG. 11B. Cryogenic cooling fluid is introduced through the catheter 150 and into the balloon 152 (in which it often vaporizes) and exhausted causing the balloon 152 to inflate, as illustrated in FIG. 11C. Because of the temperature profile of the balloon, cooling of the inner wall of the peripheral artery PA will be maximized over a central region CR and diminish in the proximal and distal directions from the central region, as illustrated qualitatively by the array of arrows in FIG. 11C. The treatment will be performed at the temperatures and for the times described thereabove in order to inhibit subsequent hyperplasia of the cells of the lining of the peripheral artery PA.

In another embodiment (which was more fully described in parent application Ser. No. 09/268,205, the full disclosure of which has been previously incorporated herein by reference) illustrated in FIG. 12, a system 310 is capable of treating a diseased vessel wall of a blood vessel using a combination of both angioplasty dilation and cryogenic cooling. In general, system 310 includes a catheter 312 coupled to a cryogenic fluid supply system 314 and an angioplasty pressurization system 316. One or both of cryogenic system 314 and pressurization system 316 may optionally be operatively coupled to a controller 318 for coordination of cooling and dilation. In some embodiments, controller 318 may actively control cryogenic cooling by modulating cooling fluid supply rates, cooling exhaust gas port pressures, cycling of the cooling fluid flow, or the like, in response to balloon pressure, measured temperature, or the like. In other embodiments, the system will be substantially self-modulating through the use of predetermined supply quantities, pressures, and/or flow cycling rates.

Catheter 312 generally includes a catheter body having a proximal end 322 and a distal end 324. A proximal housing 326 includes a number of ports for coupling of cryogenic supply system 314, pressurization system 316, and the like, to the proximal end of the catheter body. An angioplasty balloon 328 and a cryogenic balloon 330 are mounted near the distal end of catheter body 324. A catheter body will generally be flexible and contain a plurality of lumens to provide fluid communication between the ports of proximal housing 326 and balloons 328 and 330.

Angioplasty balloon 328 may be formed from a variety of materials conventionally used for dilating blood vessels. Angioplasty balloon 328 will typically comprise a nondistensible material such as polyethylene terephthalate (PET). Such angioplasty balloons are formed in a variety of sizes depending on their intended use, typically having a length and range from about 15 mm to about 50 mm and an expanded diameter in a range from about 2 mm to about 10 mm. Prior to inflation, angioplasty balloon 328 will generally remain in a low profile configuration suitable for insertion into and maneuvering through the vascular system. A guidewire lumen 332 extends through angioplasty balloon 328 and cryogenic balloon 330 from a proximal guidewire port 334 to facilitate accessing the target treatment site.

High contrast markers may be provided within balloon 328 to enhance an image of the distal end of the catheter and facilitate positioning of the balloon fluoroscopically, sonographically, or under any other alternative image modality (with appropriate contrast structures). Such markers may be formed by winding a gold or platinum wire around the tubular structure defining a pressurization lumen 336. Angioplasty balloon 328 is inflated by injecting contrast fluid 340 from pressurization system 316 into pressurization lumen 336 through a pressurization port 338. In this embodiment, balloon 328 is isolated from balloon 330, so as to avoid inadvertent inflation of the cryogenic balloon during dilation.

Figure 12:
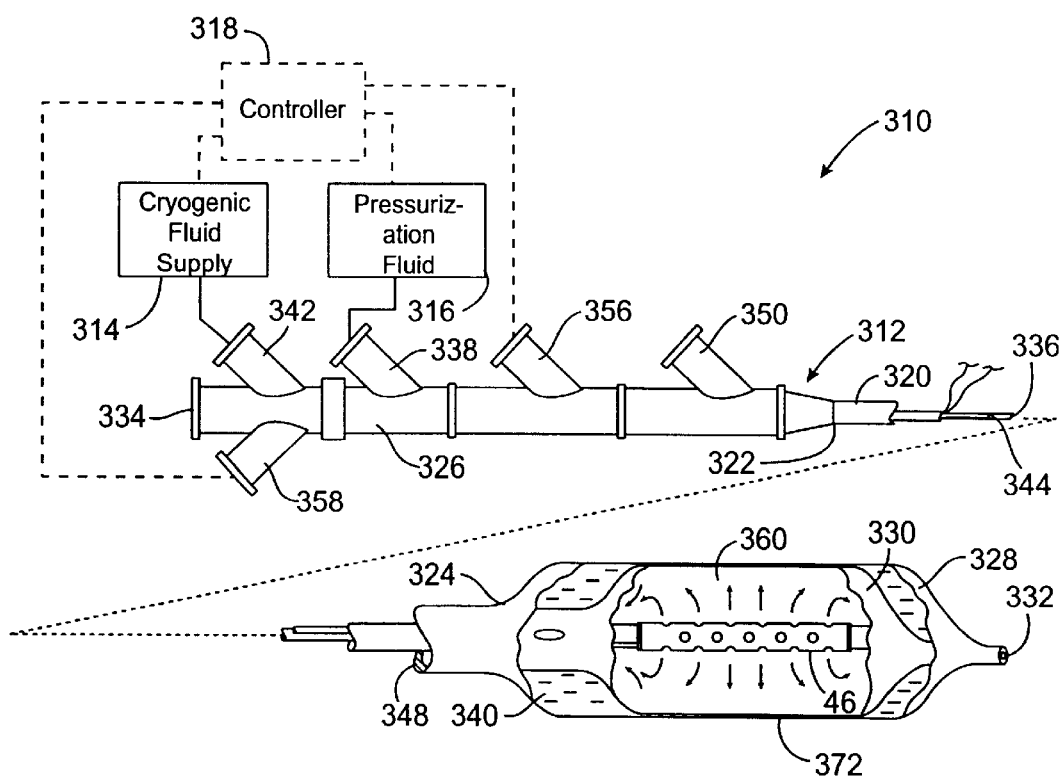
FIG. 12 schematically illustrates an alternate cryogenic/angioplasty balloon catheter system according to the principles of the present invention.

In the catheter illustrated in FIG. 12, cryogenic balloon 330 is nested within the angioplasty balloon 328. It should be understood that cryogenic balloon 330 may alternatively be axially displaced from the cryogenic balloon, or that a single balloon may function as both the cryogenic cooling and dilation. Cooling may be provided by containing the cryogenic cooling fluid within a rigid heat exchanger, and optionally cooling a surrounding balloon wall via a fluid having a predetermined freezing temperature. In still further alternative embodiments, cryogenic cooling catheters may be provided without dilation capabilities. Still further alternative cooling probes might benefit from the modulated cooling of the present invention, including hand-held probes connected to cooling surfaces by rigid shafts. In other words, many probe structures might benefit from the present invention. It should be understood that the supply system need not be separate or separable from the probe.

Regardless of the specific structure of the cooling surface, cryogenic fluid 360 is generally directed from an output of cryogenic fluid supply 314 to an input of the cooling probe. In the embodiment of FIG. 12, the cryogenic fluid is injected into a cryogenic supply port 342 and passes toward cryogenic balloon 330 through cryogenic supply lumen 344 within catheter body 320. Cryogenic fluid 360 may comprise cryogenic liquids or liquid/gas mixtures, optionally including carbon dioxide ($CO_2$), nitrous oxide ($N_2O$), a fluorocarbon such as $AZ_{-50}$™ (sold by Genetron of Morristown, N.J.), or the like. As cryogenic liquid 360 passes from the supply lumen and into cryogenic balloon 330, it may be distributed both radially and axially by a diffuser 346. Diffuser 346 will generally comprise a tubular structure with radially oriented openings. As the openings are radially oriented, diffuser 346 will direct the cooling fluid roughly perpendicularly toward the wall of cryogenic balloon 330, so that the heat transfer coefficient between the cooling vapor and balloon wall is quite even and quite high. This helps to reduce the temperature of the balloon wall, and provides greater heat extraction for a given flow rate of coolant. Additionally, as the ports are distributed both circumferentially and axially along the balloon, the diffuser can provide a substantially uniform cooling over a significant portion of (often over the majority of) the surface of the balloon.

In some embodiments, the cryogenic cooling fluid may pass through a Joule-Thompson orifice between fluid supply lumen 344 and balloon 330. In other embodiments, at least a portion of the cryogenic cooling fluid may exit one or more ports into the balloon as a liquid. The liquid will vaporize within the balloon, and the enthalpy of vaporization can help cool the surrounding vessel wall. The liquid may coat at least a portion of the balloon wall so as to enhance even cooling over at least a portion of the vessel wall. Hence, the ports of diffuser 346 may have a total cross-section which is smaller than a cross-section of the fluid supply lumen 344, or which is at least as large as (or larger than) the cross-section of the fluid supply lumen.

After the cryogenic cooling fluid vaporizes within balloon 330, it escapes the balloon proximally along an exhaust lumen 348, and is exhausted from catheter 312 through an exhaust port 350. Inflation of cryogenic balloon 330 may be controlled by the amount of cryogenic fluid injected into the balloon, and/or by the pressure head loss experienced by the exhaust gases. Cooling is generally enhanced by minimizing the pressure within balloon 330. To take advantage of this effect so as to control the amount of cooling, a fixed or variable orifice may be provided at exhaust port 350. Alternatively, a vacuum might be applied to the exhaust port to control cooling and enhance cooling efficiency. In some embodiments, a layer of insulting material 372 may be disposed between the cryogenic cooling fluid and the tissue engaging surface of the balloon. A suitable insulation material might include a thin layer of expanded Teflon™ (ePTFE) on an inner or outer surface of cryogenic balloon 330, on an inner or outer surface of angioplasty balloon 328, or the like. A wide variety of alternative insulation materials might also be used.

To accurately control and/or monitor the pressure within cryogenic balloon 330, proximal housing 326 may include a cooling balloon pressure monitoring port 356. The pressure monitoring port will be in fluid communication with the cryogenic balloon 330, preferably through a dedicated pressure monitoring lumen (not shown). Signals from pressure monitoring port 356 and a thermocouple connector 358 may be transmitted to the controller 318.

In use, the nested cryogenic/angioplasty balloon catheter of FIG. 12 may allow pre-cooling of a diseased vessel wall prior to dilation, cooling of a vessel wall after dilation, interspersed cooling/dilation, and even concurrent dilation during cooling. In some endovascular therapies, cooling without dilation may be desired, so that no provisions for inflation of an angioplasty balloon 328 by contrast 340 are required.

While the above is a complete description of the preferred embodiments of the invention, various alternatives, modifications, and equivalents will be obvious to those of skill in the art. Hence, the above description should not be taken as limiting the scope of the invention which is defined by the appended claims.

What is claimed is:

1. A cryotherapy catheter comprising:
   a catheter body having a proximal end and a distal end with a cooling fluid supply lumen and an exhaust lumen extending therebetween;
   a first balloon disposed at the distal end of the catheter body, the first balloon having an inner surface in fluid communication with the supply lumen and exhaust lumen; and
   a second balloon disposed over the first balloon with a thermal barrier therebetween, the thermal barrier comprising a gap maintained between the balloons by a filament.

2. A cryotherapy catheter as in claim 1, wherein the filament comprises helically wound, braided, woven, or knotted monofilament.

3. A cryotherapy catheter comprising:
   a catheter body having a proximal end and a distal end with a cooling fluid supply lumen and an exhaust lumen extending therebetween;
   a first balloon disposed at the distal end of the catheter body, the first balloon having an inner surface in fluid communication with the supply lumen and exhaust lumen; and
   a second balloon disposed over the first balloon with a thermal barrier therebetween, the thermal barrier comprising a gap maintained between the balloons by a plurality of bumps on an outer surface of the first balloon.

4. A cryotherapy catheter comprising:
   a catheter body having a proximal end and a distal end with a cooling fluid supply lumen and an exhaust lumen extending therebetween;
   a first balloon disposed at the distal end of the catheter body, the first balloon having an inner surface in fluid communication with the supply lumen and exhaust lumen; and
   a second balloon disposed over the first balloon with a thermal barrier therebetween, the thermal barrier comprising a gap maintained between the balloons by a plurality of bumps on an inner surface of the second balloon.

5. A cryotherapy catheter comprising:
   a catheter body having a proximal end and a distal end with a cooling fluid supply lumen and an exhaust lumen extending therebetween;
   a first balloon disposed at the distal end of the catheter body, the first balloon having an inner surface in fluid communication with the supply lumen and exhaust lumen; and
   a second balloon disposed over the first balloon with a thermal barrier therebetween, the thermal barrier comprising a gap maintained between the balloons by a sleeve.

6. A cryotherapy catheter comprising:
   a catheter body having a proximal end and a distal end with a cooling fluid supply lumen and an exhaust lumen extending therebetween;
   a first balloon disposed at the distal end of the catheter body, the first balloon having an inner surface in fluid communication with the supply lumen and exhaust lumen;
   a second balloon disposed over the first balloon with a thermal barrier therebetween; and
   a reinforcing coil extending along the catheter body proximal of the first balloon.

7. A cryotherapy catheter comprising:
   a catheter body having a proximal end and a distal end with a cooling fluid supply lumen and an exhaust lumen extending therebetween;
   a first balloon disposed at the distal end of the catheter body, the first balloon having an inner surface in fluid communication with the supply lumen and exhaust lumen;
   a second balloon disposed over the first balloon with a thermal barrier therebetween; and
   a guidewire lumen in the catheter body that extends axially outside the exhaust lumen.

8. A cryotherapy catheter comprising:
   a catheter body having a proximal end and a distal end with a cooling fluid supply lumen and an exhaust lumen extending therebetween;
   a first balloon disposed at the distal end of the catheter body, the first balloon having an inner surface in fluid communication with the supply lumen and exhaust lumen;
   a second balloon disposed over the first balloon with a thermal barrier therebetween; and
   a vacuum means for reducing a fluid pressure between the first and second balloons.

9. A cryotherapy catheter comprising:
   a catheter body having a proximal end and a distal end with a cooling fluid supply lumen and exhaust lumen extending therebetween;
   a balloon disposed at the distal end of the catheter body, the balloon having an inner surface in fluid communication with the supply lumen and exhaust lumen; and
   an elastic membrane disposed over the balloon with a thermal barrier therebetween.

10. A cryotherapy system comprising:
    an elongate body having a proximal end and a distal end with a fluid supply lumen and an exhaust lumen extending therebetween;

a first balloon defining a volume in fluid communication with the supply lumen and the exhaust lumen;

a cryogenic fluid supply;

a fluid shutoff coupling the cryogenic fluid supply with the supply lumen; and a second balloon disposed over the first balloon with a vacuum space therebetween, the vacuum space coupled to the fluid shutoff so as to inhibit flow of cryogenic fluid into the first balloon in response to a change in the vacuum space.

11. A cryotherapy system of claim 10, wherein the fluid shutoff is a vacuum switch connected to a shutoff valve by a circuit.

12. A cryotherapy system of claim 11, further comprising an energy pack including the cryogenic fluid supply and a battery for powering the circuit, wherein the energy pack is detachable from the body and is disposable.

13. A cryotherapy system of claim 10, wherein the cryogenic fluid supply comprises a plurality of separate replaceable energy packs to allow for multiple cryogenic fluid cooling cycles.

14. A cryotherapy system of claim 10, further comprising a hypsometer coupled to the volume to determine at least one of a pressure and temperature of fluid within the first balloon.

15. A cryotherapy system of claim 14, wherein the hypsometer is a thermocouple.

16. A cryotherapy system of claim 10, further comprising a reinforcing coil extending along the body proximal of the first balloon.

17. A cryotherapy system of claim 10, further comprising a guidewire lumen in the body that extends axially outside the exhaust lumen.

18. A cryotherapy system of claim 10, further comprising a thermal barrier disposed between the first and second balloons so as to limit cooling.

19. A cryotherapy catheter comprising:

a catheter body having a proximal end and a distal end with a nebulizer disposed adjacent the distal end; and a first balloon disposed on the distal end of the catheter body, the first balloon having an inner surface in fluid communication with the nebulizer.

20. A cryotherapy catheter as in claim 19, wherein the nebulizer comprises at least one port in fluid communication with a liquid supply lumen and a gas supply lumen.

21. A cryotherapy catheter as in claim 20, wherein the liquid supply lumen is coaxial with the gas supply lumen.

22. A cryotherapy catheter as in claim 20, wherein a portion of liquid from the liquid supply lumen is atomized in the balloon and another portion of liquid returns toward the proximal end of the catheter from the balloon.

23. A cryotherapy catheter as in claim 19, further comprising a reinforcing coil extending along the catheter body proximal of the balloon.

24. A cryotherapy catheter as in claim 19, further comprising a guidewire lumen that extends axially outside the nebulizer.

25. A cryotherapy catheter as in claim 19, further comprising:

a second balloon disposed over the first balloon; and a thermal barrier between the first and second balloons to limit cooling.

26. A cryotherapy catheter as in claim 19, further comprising:

a second balloon disposed over the first balloon with a vacuum space therebetween; and a fluid shutoff on the proximal end of the catheter body, the fluid shutoff coupled to the nebulizer and the vacuum space so as to inhibit the flow of fluid into the first balloon in response to a change in the vacuum space.

27. A method for treating a target portion of a blood vessel, the method comprising:

positioning a first balloon within the blood vessel adjacent the target portion;

introducing a cryogenic cooling fluid into the first balloon;

exhausting the cooling fluid;

expanding a second balloon disposed over the first balloon to radially engage the vessel wall;

cooling the target portion to a temperature and for a time sufficient to inhibit subsequent cell growth; and inhibiting heat transfer between the first and second balloons so as to limit cooling of the target portion.

28. A method for treating a target portion of a blood vessel, the method comprising:

positioning a first balloon within the blood vessel adjacent the target portion;

introducing a cryogenic cooling fluid into the first balloon;

exhausting the cooling fluid;

expanding a second balloon disposed over the first balloon to radially engage the vessel wall;

cooling the target portion to a temperature and for a time sufficient to inhibit subsequent cell growth; and monitoring the containment of the first and second balloons during cooling.

29. A method as in claim 28, wherein the monitoring step is carried out by an automatic fluid shutoff mechanism.

30. A method for treating a target portion of a blood vessel, the method comprising:

positioning a balloon within the blood vessel adjacent the target portion;

introducing a cryogenic liquid and gas mixture into the balloon with a nebulizer;

exhausting the cryogenic liquid and gas mixture; and cooling the target portion to a temperature and for a time sufficient to inhibit subsequent cell growth.

* * * * *

UNITED STATES PATENT AND TRADEMARK OFFICE
CERTIFICATE OF CORRECTION

PATENT NO. : 6,514,245 B1  
DATED : February 4, 2003  
INVENTOR(S) : Timothy Holland et al.

Page 1 of 1

It is certified that error appears in the above-identified patent and that said Letters Patent is hereby corrected as shown below:

<u>Title page,</u>
Item [75], the corrected list of inventors should read as follows:
-- [75]  Inventors:  Timothy D. Holland, Los Gatos, CA (US); Ronald Williams, Menlo Park, CA (US); James Joye, Los Gatos, CA (US); Richard S. Williams, Redwood City, CA (US) --
Item [12], the corrected Patent heading should read as follows:
-- [12]  United States Patent
      Holland et al. --

Signed and Sealed this

Seventh Day of October, 2003

JAMES E. ROGAN  
*Director of the United States Patent and Trademark Office*